(12) United States Patent
Riley et al.

(10) Patent No.: US 9,238,601 B2
(45) Date of Patent: Jan. 19, 2016

(54) METHOD FOR PROVIDING OXYGEN FREE REGENERATION GAS FOR NATURAL GAS DRYERS

(71) Applicant: UOP LLC, Des Plaines, IL (US)

(72) Inventors: Mark G. Riley, Hinsdale, IL (US); Shain-Jer Doong, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 296 days.

(21) Appl. No.: 14/054,070

(22) Filed: Oct. 15, 2013

(65) Prior Publication Data
US 2015/0105599 A1 Apr. 16, 2015

(51) Int. Cl.
*C07C 7/12* (2006.01)
*C10L 3/00* (2006.01)
*C10L 3/10* (2006.01)

(52) U.S. Cl.
CPC ... *C07C 7/12* (2013.01); *C10L 3/00* (2013.01); *C10L 3/101* (2013.01)

(58) Field of Classification Search
None
See application file for complete search history.

(56) References Cited

U.S. PATENT DOCUMENTS

| | | | |
|---|---|---|---|
| 6,387,337 B1 | 5/2002 | Pennline et al. | |
| 7,368,409 B2 | 5/2008 | Robinson et al. | |
| 8,431,081 B2 | 4/2013 | Demirel et al. | |
| 2007/0249879 A1* | 10/2007 | Iaccino | C07C 2/78 585/418 |
| 2010/0028229 A1 | 2/2010 | Carnell et al. | |
| 2012/0083637 A1* | 4/2012 | Clem | B01J 29/48 585/415 |

FOREIGN PATENT DOCUMENTS

| | | |
|---|---|---|
| EP | 1 345 693 B1 | 9/2003 |
| WO | WO 2008/107709 A1 | 9/2008 |

* cited by examiner

*Primary Examiner* — Tam M Nguyen

(57) ABSTRACT

Methods of removing free oxygen from a hydrocarbon stream are described. A hydrocarbon stream containing free oxygen is contacted with an adsorbent comprising a metal in a reduced state. The free oxygen in the hydrocarbon stream reacts with the metal in the reduced state to form oxidized metal and a reduced oxygen hydrocarbon stream. Syngas is made from a portion of the reduced oxygen hydrocarbon stream. A regeneration gas stream comprising a mixture of the syngas and another portion of the reduced oxygen hydrocarbon stream is contacted with the oxidized metal to reduce the oxidized metal to form the metal in the reduced state.

20 Claims, 2 Drawing Sheets

METHOD FOR PROVIDING OXYGEN FREE REGENERATION GAS FOR NATURAL GAS DRYERS

BACKGROUND OF THE INVENTION

Natural gas generally refers to light gaseous hydrocarbons, and especially comprising methane. Natural gas also contains hydrocarbons such as ethane, propane, butanes, and the like, along with inert components, such as nitrogen, argon, and carbon dioxide. Natural gas is recovered from underground reservoirs, and is commonly used as an energy source for heating and power generation. Typically, natural gas is recovered at high pressure, processed, and fed into a gas pipeline under pressure.

As gas wells age and their natural pressure drops, oxygen infiltration becomes more of a problem. It is well known that oxygen contamination of natural gas used for regeneration of the molecular sieve drying unit can lead to damage of the molecular sieves through combustion of residual heavy hydrocarbon. Oxygen can easily be removed from natural gas using a transition metal based adsorbent, such as a copper based adsorbent. Reduced copper can decrease the oxygen concentration to very low levels at ambient temperature.

The copper based adsorbent is regenerable provided a suitable reducing gas can be obtained. Unfortunately, most natural gas facilities do not have a stream capable of reducing CuO at temperatures below 287.8° C. (550° F.), the maximum temperature usually available in natural gas plants.

Therefore, there is a need for processes for treating natural gas to remove oxygen at the lower temperatures available in natural gas processing plants.

SUMMARY OF THE INVENTION

On aspect of the present invention is a method of removing free oxygen from a hydrocarbon stream. In one embodiment, the method includes contacting the hydrocarbon stream with an adsorbent in an oxygen removal zone. The adsorbent comprises a metal in a reduced state. The free oxygen in the hydrocarbon stream reacts with the metal in the reduced state to form oxidized metal and a reduced oxygen hydrocarbon stream. A portion of the reduced oxygen hydrocarbon stream is removed, and reacted to form a gas mixture comprising hydrogen. The gas mixture is combined with a second portion of the reduced oxygen hydrocarbon stream to form a regeneration gas stream. The regeneration gas stream is contacted with the oxidized metal to reduce the oxidized metal to form the metal in the reduced state and a spent regeneration gas stream.

DETAILED DESCRIPTION OF THE INVENTION

Oxygen contamination in the regenerant gas stream to a natural gas dryer is greatly reduced by the addition of a bed of adsorbent capable of adsorbing oxygen from natural gas. The adsorbent typically is based on a metal oxide that is reduced and then easily oxidized by the oxygen present in natural gas. The adsorbent is regenerated by passing a reducing gas over the adsorbent, converting the metal oxide back to reduced metal. Adsorbents based on copper are often used for oxygen removal, but other transition metals can also be used. The reducing gas can be produced using a small scale plant to produce syngas by partial oxidation of methane, steam reforming, or catalytic dehydrogenation.

The oxygen adsorbent removes oxygen from the natural gas stream to the dryer before it passes over the molecular sieves. Oxygen removal adsorbent is regenerated using hydrogen/carbon monoxide syngas at 287.8° C. (550° F.) or lower.

Figure 1:
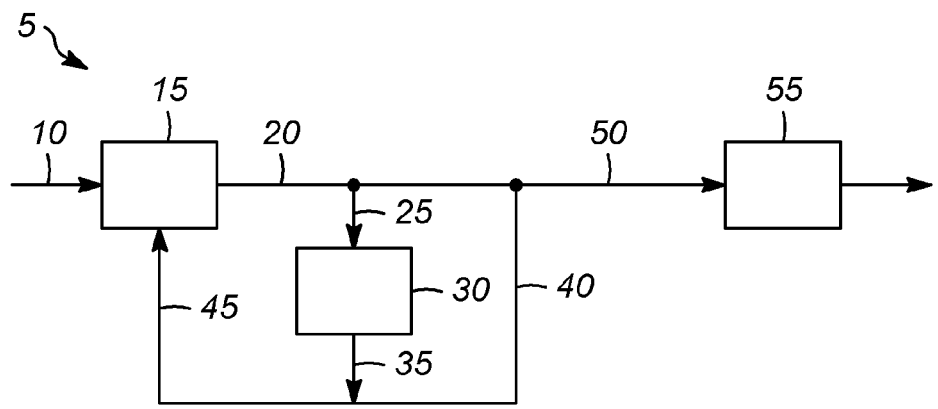
FIG. 1 is an illustration of one embodiment of a process for removing free oxygen from a hydrocarbon stream.

One embodiment of the process 5 is illustrated in FIG. 1. The hydrocarbon stream 10 is contacted with an adsorbent in an oxygen removal zone 15. The adsorbent comprises a metal in a reduced state. The metal is typically one or more transition metals from Groups 8-12 (IUPAC) of the Periodic Table. Commonly, the metal is Fe, Co, Ni, Cu, Zn, or combinations thereof. For example, copper based adsorbents for removal of oxygen are commercially available from UOP LLC, BASF, and other companies.

The free oxygen in the hydrocarbon stream 10 reacts with the metal in the reduced state to form oxidized metal, which produces a hydrocarbon stream 20 having a reduced level of free oxygen compared to the incoming hydrocarbon stream 10. The initial level of free oxygen will typically be less than 150 ppm, or less than about 125 ppm, or less than about 100 ppm. Although the initial level can be higher, it may be more economical to remove the oxygen using other methods, such as catalytic combustion, at higher oxygen levels. The level of free oxygen can reduced to less than about 20 ppm, or less than about 15 ppm, or less than about 10 ppm, or less than about 5 ppm, or less than about 3 ppm, or less than about 1 ppm.

The oxygen regeneration zone typically operates at room temperature to about 130° C., atmospheric pressure to about 5 MPa (g) (50 bar (g)), and space velocity of about 1,000 to about 1,500 $hr^{-1}$.

The adsorbent also removes sulfur compounds, such as $H_2S$, COS, mercaptans, COS, $CS_2$, and arsine (if present), and phosphine (if present).

A portion 25 of the hydrocarbon stream 20 is sent to a reaction zone 30 where it is reacted to form a gas mixture 35 comprising hydrogen. The amount of gas mixture needed is a function of a number of factors including the size of the bed and the amount of CuO formed. One mole of hydrogen or carbon monoxide is needed to reduce one mole of CuO.

The gas mixture comprising hydrogen is typically synthesis gas (syngas). Syngas can be formed from the portion of the reduced oxygen hydrocarbon stream using known processes, including one or more of: partially oxidation, steam reforming, and catalytic dehydrogenation.

Steam reforming involves reacting methane and steam to form carbon monoxide and hydrogen. Steam reforming is energy intensive in that the process consumes over 200 kJ/mole of methane consumed and therefore requires a furnace or other source of continuous heat.

Partial oxidation comprises burning methane in an oxygen lean environment where the methane is partially oxidized to carbon monoxide along with the production of hydrogen and some steam. Partial oxidation is exothermic and yields a significant amount of heat. Because one reaction is endothermic and the other is exothermic, these reactions are often performed together for efficient energy usage. Combining the steam reforming and partial oxidation yields a third process wherein the heat generated by the partial oxidation is used to drive the steam reforming to yield a syngas. However, the partial oxidation needs a higher concentration of oxygen than is found in air, and the energy associated with the separation of air off-sets the advantage of the energy needed for steam reforming.

Processes for syngas formation by partial oxidation and stream reforming are well known and can be found in U.S. Pat. No. 7,262,334 and U.S. Pat. No. 7,226,548, and are incorporated by reference in their entirety.

Syngas from partial oxidation and/or stream reforming comprises carbon monoxide (CO), water ($H_2O$), and hydrogen ($H_2$).

Catalytic dehydrogenation involves the dehydrogenation of alkanes over a dehydrogenation catalyst (e.g., platinum group metals) to generate olefins and hydrogen.

The gas mixture 35 is combined with a second portion 40 of the hydrocarbon stream 20 to form a regeneration gas stream 45. The regeneration gas stream 45 is contacted with the oxidized metal to reduce the metal to regenerate the adsorbent by re-forming the metal in the reduced state. The length of time for regeneration depends on the amount of oxygen to be removed, the effect of the regeneration conditions, with shorter times requiring harsher conditions which may have a negative effect on the adsorbent, and plant conditions and limitations.

The rest of the hydrocarbon stream 50 is sent for further processing, such as to dryer 55. Thereafter, it could be sent to a pipeline for distribution. Alternatively, it could be liquefied and transported.

Copper based materials used in oxygen removal service have a fairly high metal content, and if the amount of hydrogen in the regeneration gas is not controlled, large exotherms can occur. Temperature excursions can result in the loss of oxygen capacity because of copper's tendency to sinter easily due to its low melting point.

The regeneration of the adsorbent is controlled by determining the amount of hydrogen and carbon monoxide in the gas mixture. The maximum amount of hydrogen and carbon monoxide so that a temperature in the regeneration zone does not exceed about 230° C. is also determined. The amount of the gas mixture 35 and the amount of the second portion 40 of the reduced oxygen hydrocarbon stream is controlled so that the amount of hydrogen and carbon monoxide in the regeneration gas stream does not exceed the maximum amount of hydrogen and carbon monoxide. The concentration of reducing gas is typically not more than about 0.5% at the start of the process. The concentration can be increased as the regeneration process continues, up to about 20% at the end of the process. When the regeneration is first performed, a low gas concentration is used initially (e.g., about 0.5%), and the exotherm is observed. If the maximum temperatures are not exceeded, the amount of reducing gas can be increased, which will shorten the regeneration cycle. This process can be repeated to provide a plan for increasing the amount of reducing gas in future regeneration cycles.

Using the natural gas with the reduced oxygen content as a diluent allows a fairly high flow rate to be used to remove heat, and the amount of reducing gas can be controlled to prevent temperature excursions. If syngas from the partial oxidation unit (or other syngas producing process) is used for regeneration without any dilution, then it is hard to maintain the high flow for heat removal and to manage the amount of reducing gas present to control the exotherm.

The regeneration process can take place periodically, if desired. In this arrangement, the hydrocarbon stream 10 would be contacted with the adsorbent until the adsorbent is spent. This would initiate the regeneration cycle of removing the portion of the reduced oxygen hydrocarbon stream, reacting the portion of the reduced oxygen hydrocarbon stream, combining the gas mixture with the second portion of the reduced oxygen hydrocarbon stream, and contacting the regeneration gas stream with the oxidized metal.

In some embodiments, the hydrocarbon stream can be contacted with the adsorbent continuously. This can be done using a swing bed arrangement, for example. The oxygen removal zone can comprise at least two beds. The hydrocarbon stream is contacted with the adsorbent in the first bed until the adsorbent in the first bed is spent. After the first bed is spent, the hydrocarbon stream is contacted with the adsorbent in the second bed. The first bed can then undergo regeneration.

Figure 2:
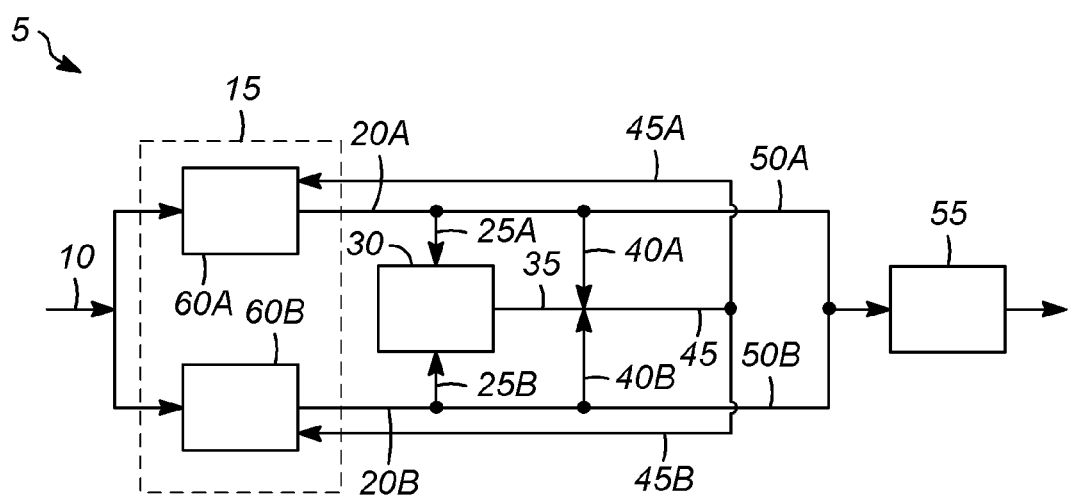
FIG. 2 is an illustration of another embodiment of a process for removing free oxygen from a hydrocarbon stream.

FIG. 2 illustrates one embodiment of a process 5 utilizing an oxygen removal zone 15 containing at least two beds 60A and 60B. The hydrocarbon feed 10 can be sent to either bed 60A or 60B. The hydrocarbon feed 10 is first sent to bed 60A until it becomes spent. After the adsorbent in the first bed 60A is spent, the hydrocarbon feed 10 is sent to the second bed 60B.

When the hydrocarbon feed 10 is switched to bed 60B, the regeneration of bed 60A is initiated. In this embodiment, the regeneration equipment is shared between the two beds 60A and 60B. A portion 25B of the hydrocarbon stream 20B is removed and sent to the reaction zone 30 where it is reacted to form the gas mixture 35. The gas mixture 35 is combined with a second portion 40B of the hydrocarbon stream 20B to form a regeneration gas stream 45, which is then sent to regenerate bed 60A. The rest of the hydrocarbon stream 50B is sent for further processing, such as to dryer 55. The same process would occur to regenerate bed 60B using portions 25A and 40A.

Figure 3:
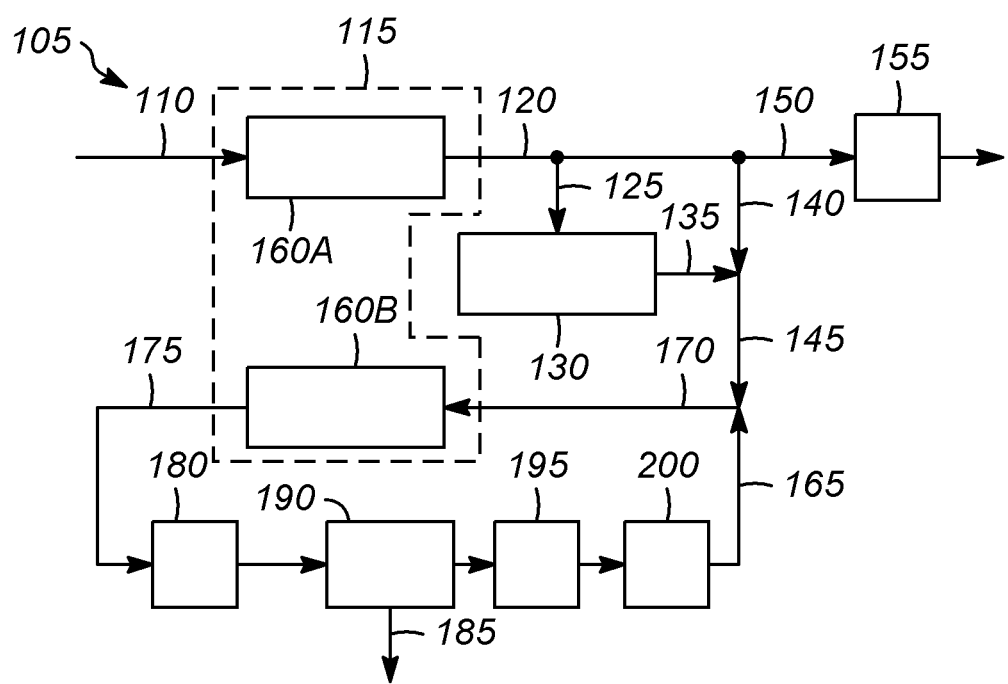
FIG. 3 is an illustration of another embodiment of a process for removing free oxygen from a hydrocarbon stream.

FIG. 3 illustrates another embodiment of a process 105 utilizing recycle of the spent regeneration gas. As illustrated in FIG. 3, the hydrocarbon feed 110 is sent to an oxygen removal zone 115 having two beds 160A and 160B. However, the oxygen removal zone could have one or more beds, as desired.

As shown in FIG. 3, the hydrocarbon feed 110 is being sent to bed 160A, and bed 160B is undergoing regeneration. A portion 125 of the hydrocarbon stream 120 is sent to the reaction zone 130 where it is reacted to form the gas mixture 135. The gas mixture 135 is combined with a second portion 140 of the hydrocarbon stream 120 to form a regeneration gas stream 145, which is then sent to regenerate bed 160B. The rest of the hydrocarbon stream 150 is sent for further processing, such as to dryer 155.

The regeneration gas stream 145 is combined with treated spent regeneration gas stream 165 to form stream 170 which is used to regenerate the bed 160B. The spent regeneration gas stream 175 is sent to one or more process units. The spent regenerated gas stream 175 is cooled in cooling unit 180. Water 185 is removed from the spent regenerated gas stream in condensing unit 190. The pressure is increased in blower unit 195. The temperature is raised in heating unit 200. Recycling the spent regeneration gas minimizes product gas loss and reduces the amount of portion 140 (make up gas) needed. It also allows recovery of the unused hydrogen and/or carbon monoxide gas.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of removing free oxygen from a hydrocarbon stream comprising:
   contacting the hydrocarbon stream with an adsorbent in an oxygen removal zone, the adsorbent comprising a metal in a reduced state, the free oxygen in the hydrocarbon stream reacting with the metal in the reduced state to form oxidized metal and a reduced oxygen hydrocarbon stream;
   removing a portion of the reduced oxygen hydrocarbon stream;
   reacting the portion of the reduced oxygen hydrocarbon stream to form a gas mixture comprising hydrogen;
   combining the gas mixture with a second portion of the reduced oxygen hydrocarbon stream to form a regeneration gas stream;
   contacting the regeneration gas stream with the oxidized metal to reduce the oxidized metal to form the metal in the reduced state and a spent regeneration gas stream.

2. The method of claim 1 wherein combining the gas mixture with the second portion of the reduced oxygen hydrocarbon stream to form the regeneration gas stream comprises:
   determining an amount of hydrogen and carbon monoxide in the gas mixture;
   determining a maximum amount of hydrogen and carbon monoxide so that a temperature during regeneration does not exceed about 230° C.; and
   controlling an amount of the gas mixture and an amount of the second portion of the reduced oxygen hydrocarbon stream so that the amount of hydrogen and carbon monoxide in the regeneration gas stream does not exceed the maximum amount of hydrogen and carbon monoxide.

3. The method of claim 1 wherein reacting the portion of the reduced oxygen hydrocarbon stream comprises one or more of partially oxidizing the portion of the reduced oxygen hydrocarbon stream, steam reforming the portion of the reduced oxygen hydrocarbon stream, or catalytically dehydrogenating the portion of the reduced oxygen hydrocarbon stream.

4. The method of claim 1 wherein the metal is a transition metal from Groups 8-12 of the Periodic Table, or combinations thereof.

5. The method of claim 1 wherein the metal is Fe, Co, Ni, Cu, Zn, or combinations thereof.

6. The method of claim 1 wherein removing the portion of the reduced oxygen hydrocarbon stream, reacting the portion of the reduced oxygen hydrocarbon stream, combining the gas mixture with the second portion of the reduced oxygen hydrocarbon stream, and contacting the regeneration gas stream with the oxidized metal take place periodically.

7. The method of claim 6 wherein contacting the hydrocarbon stream with the adsorbent takes place continuously.

8. The method of claim 1 wherein the oxygen removal zone comprises at least two beds, and wherein the hydrocarbon stream is contacted with the adsorbent in the first bed until the adsorbent in the first bed is spent, and after the first bed is spent, the hydrocarbon stream is contacted with the adsorbent in the second bed.

9. The method of claim 8 wherein when the hydrocarbon stream is contacted with the adsorbent in the second bed, the steps of removing the portion of the reduced oxygen hydrocarbon stream, reacting the portion of the reduced oxygen hydrocarbon stream, combining the gas mixture with the second portion of the reduced oxygen hydrocarbon stream, and contacting the regeneration gas stream with the oxidized metal are initiated.

10. The method of claim 1 further comprising combining the spent regeneration gas stream with the regeneration gas stream before contacting the regeneration gas stream with the oxidized metal.

11. The method of claim 10 further comprising treating the spent regeneration gas stream with at least one process before combining the spent regeneration gas stream with the regeneration gas stream, the at least one process selected from cooling the spent regeneration gas stream, removing water from the spent regeneration gas stream, increasing the pressure of the spent regeneration gas stream, and heating the spent regeneration gas stream.

12. A method of removing free oxygen from a hydrocarbon stream comprising:
   contacting the hydrocarbon stream with an adsorbent in an oxygen removal zone, the adsorbent comprising a metal in a reduced state, the free oxygen in the hydrocarbon stream reacting with the metal in the reduced state to form oxidized metal and a reduced oxygen hydrocarbon stream;
   removing a portion of the reduced oxygen hydrocarbon stream;
   reacting the portion of the reduced oxygen hydrocarbon stream to form a gas mixture comprising hydrogen;
   determining an amount of hydrogen and carbon monoxide in the gas mixture;
   determining a maximum amount of hydrogen and carbon monoxide so that a temperature during regeneration does not exceed about 230° C.;
   combining the gas mixture with a second portion of the reduced oxygen hydrocarbon stream to form a regeneration gas stream;
   controlling an amount of the gas mixture and an amount of the second portion of the reduced oxygen hydrocarbon stream so that the amount of hydrogen and carbon monoxide in the regeneration gas stream does not exceed the maximum amount of hydrogen and carbon monoxide; and
   contacting the regeneration gas stream with the oxidized metal to reduce the oxidized metal to form the metal in the reduced state and a spent regeneration stream.

13. The method of claim 12 wherein reacting the portion of the reduced oxygen hydrocarbon stream comprises one or more of partially oxidizing the portion of the reduced oxygen hydrocarbon stream, steam reforming the reduced oxygen hydrocarbon stream, or catalytically dehydrogenating the reduced oxygen hydrocarbon stream.

14. The method of claim 12 wherein the metal is a transition metal from Groups 8-12 of the Periodic Table, or combinations thereof.

15. The method of claim 12 wherein the metal is Fe, Co, Ni, Cu, Zn, or combinations thereof.

16. The method of claim 12 wherein removing the portion of the reduced oxygen hydrocarbon stream, reacting the portion of the reduced oxygen hydrocarbon stream, combining the gas mixture with the second portion of the reduced oxygen hydrocarbon stream, and contacting the regeneration gas stream with the oxidized metal take place periodically.

17. The method of claim 16 wherein contacting the hydrocarbon stream with the adsorbent takes place continuously.

18. The method of claim 12 wherein the oxygen removal zone comprises at least two beds, and wherein the hydrocarbon stream is contacted with the adsorbent in the first bed until the adsorbent in the first bed is spent, and after the first bed is spent, the hydrocarbon stream is contacted with the adsorbent in the second bed.

19. The method of claim 18 wherein when the hydrocarbon stream is contacted with the adsorbent in the second bed, the steps of removing the portion of the reduced oxygen hydrocarbon stream, reacting the portion of the reduced oxygen hydrocarbon stream, combining the gas mixture with the second portion of the reduced oxygen hydrocarbon stream, and contacting the regeneration gas stream with the oxidized metal are initiated.

20. The method of claim 12 further comprising:
- treating the spent regeneration gas stream with at least one process selected from cooling the spent regeneration gas stream, removing water from the spent regeneration gas stream, increasing the pressure of the spent regeneration gas stream, and heating the spent regeneration gas stream to form a treated spent regeneration stream; and
- combining the treated spent regeneration gas stream with the regeneration gas stream before contacting the regeneration gas stream with the oxidized metal.

* * * * *